United States Patent
Mitchell

(10) Patent No.: US 9,835,616 B2
(45) Date of Patent: Dec. 5, 2017

(54) IN VITRO METHOD FOR ASSESSING CYTOKINE STORM RESPONSES

(71) Applicant: IMPERIAL INNOVATIONS LTD., London (GB)

(72) Inventor: Jane Alison Mitchell, London (GB)

(73) Assignee: Imperial Innovations Ltd., London (GB)

( * ) Notice: Subject to any disclaimer, the term of this patent is extended or adjusted under 35 U.S.C. 154(b) by 0 days.

(21) Appl. No.: 14/778,729

(22) PCT Filed: Mar. 21, 2014

(86) PCT No.: PCT/EP2014/055695
§ 371 (c)(1),
(2) Date: Sep. 21, 2015

(87) PCT Pub. No.: WO2014/147216
PCT Pub. Date: Sep. 25, 2014

(65) Prior Publication Data
US 2016/0047795 A1    Feb. 18, 2016

(30) Foreign Application Priority Data

Mar. 22, 2013 (GB) .................................. 1305318.6
May 24, 2013 (GB) .................................. 1309385.1

(51) Int. Cl.
*A61K 38/00* (2006.01)
*A61K 39/00* (2006.01)
*G01N 33/50* (2006.01)

(52) U.S. Cl.
CPC ..... *G01N 33/5023* (2013.01); *G01N 33/5047* (2013.01); *G01N 2333/52* (2013.01)

(58) Field of Classification Search
CPC ....................... G01N 33/5023; G01N 33/5047
See application file for complete search history.

(56) References Cited

U.S. PATENT DOCUMENTS

2011/0082091 A1* 4/2011 Hunig ................ C07K 16/2818
514/20.5

FOREIGN PATENT DOCUMENTS

WO    WO2011036308    3/2011

OTHER PUBLICATIONS

Stebbings et al., (J Immunol. 2007;179:3325-3331).*
Findlay et al., (Cytokine Jul. 2011;55(1):141-51. Epub Apr. 13, 2011).*
Bland et al., (BMJ 1994:309;1128).*
Walker et al., (Int Immunopharmacol. 2011;11:1697-1705).*
(Continued)

*Primary Examiner* — Cherie M Stanfield
(74) *Attorney, Agent, or Firm* — Saul Ewing Arnstein & Lehr LLP; Debora Plehn-Dujowich

(57) ABSTRACT

The present disclosure an in vitro method of assaying the stimulation of a cytokine storm response comprising the steps of: a. co-culturing PBMCs and matched differentiated endothelial cells to provide a system representative of human responses in vivo, and b. exposing the co-cultured cell system to a test agent, c. analyzing the system for the presence of one or more cytokines released after exposing the co-culture system to said test agent, and d. optionally evaluating the response to the test agent in comparison to a response to one or more control agents.

9 Claims, 8 Drawing Sheets

(56) References Cited

OTHER PUBLICATIONS

Figure 5A:
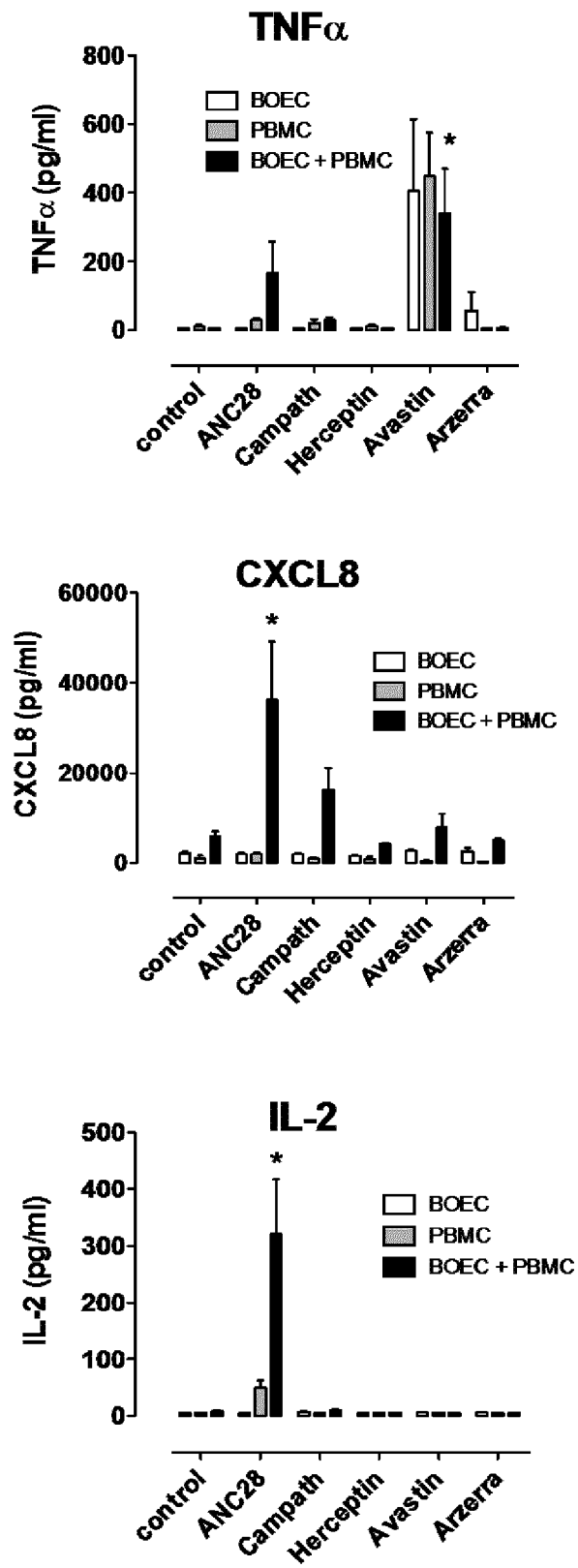

Martin-Ramirez et al., (Nature Protocols. Sep. 2012. 7:1709-1715. ePub Aug. 23, 2012).*

Stebbings R, et al., "Cytokine storm" in the phase I trial of monoclonal antibody TGN1412: better understanding the causes to improve preclinical testing of immune therapeutics., J Immunol. ,179:3325-31 (2007).

Walker MR, et al., Development of a human whole blood assay for prediction of cytokine release similar to anti-CD28 superagonists using multiplex cytokine and hierarchical cluster analysis, Int Immunopharmaco1,11:1697-705 (2011).

Bailey L, et al., A simple whole blood bioassay detects cytokine responses to anti-CD28(SA) and anti-CD52 antibodies, J Pharmacol Toxicol Methods (2012).

Findlay L, et al., Comparison of novel methods for predicting the risk of pro-inflammatory clinical infusion reactions during monoclonal antibody therapy, J Immunol Methods,371:134-42 (2011).

Eastwood D, et al., Monoclonal antibody TGN1412 trial failure explained by species differences in CD28 expression on CD4+ effector memory T-celis. Br J Pharmacal,161:512-26 (2011).

Hünig T. The storm has cleared: lessons from the CD28 superagonist TGN1412 trial. Nat Rev Immunol, 12:317-8 (2012).

Finco D, et al., Cytokine release assays: Current practices and future directions, Cytokine,66:143-55 (2014).

Földes, G, et al., Innate immunity in human embryonic stem cells: comparison with adult human endothelial cells, PLoS One, 5:e10501 (2010).

Yoder MC, et al., Redefining endothelial progenitor cells via clonal analysis and hematopoietic stem/progenitor cell principals, Blood, 109:1801-9 (2007).

Ingram DA, et al., Identification of a novel hierarchy of endothelial progenitor cells using human peripheral and umbilical cord blood, Blood,104:2752-60 (2004).

Paschalaki KE, et al., Dysfunction of endothelial progenitor cells from smokers and chronic obstructive pulmonary disease patients due to increased DNA damage and senescence, Stem Cells, 31:2813-26 (2013).

George PM, et al., Evidence for the Involvement of Type I Interferon in Pulmonary Arterial Hypertension, Circ Res (2013).

Potter CM, et al., Role of shear stress in endothelial cell morphology and expression of cyclooxygenase isoforrns. Arterioscler Thromb Vase Biol, 31:384-91 (2011).

Martin-Ramirez J, et al., Establishment of outgrowth endothelial cells from peripheral blood, Nat Protoc, 7:1709-15 (2012).

Thill M, et al., Late outgrowth endothelial progenitor cells in patients with age-related macular degeneration, Invest Ophthalmol Vis Sci, 49:2696-708 (2008).

Suntharalingam G, et al., Cytokine storm in a phase 1 trial of the anti-CD28 monoclonal antibody TGN1412, N Engl J Med,355:1018-28 (2006).

Stebbings R, et al., After TGN1412: Recent developments in cytokine release assays, J Immunotoxicol (2012).

Dhir V, et al., A predictive biomimetic model of cytokine release induced by TGN1412 and other therapeutic monoclonal antibodies, J Immunotoxicol, 9:34-42 (2012).

Huang, et al., Alloantigenitcity of human endothelial cells, Translplantation, 57:703-711 (1994).

* cited by examiner

Figure 1A, B & C
A
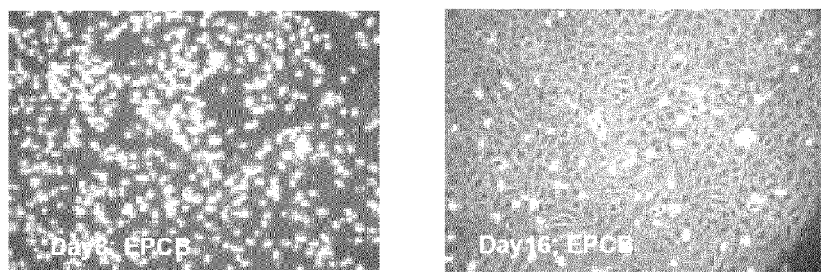
B
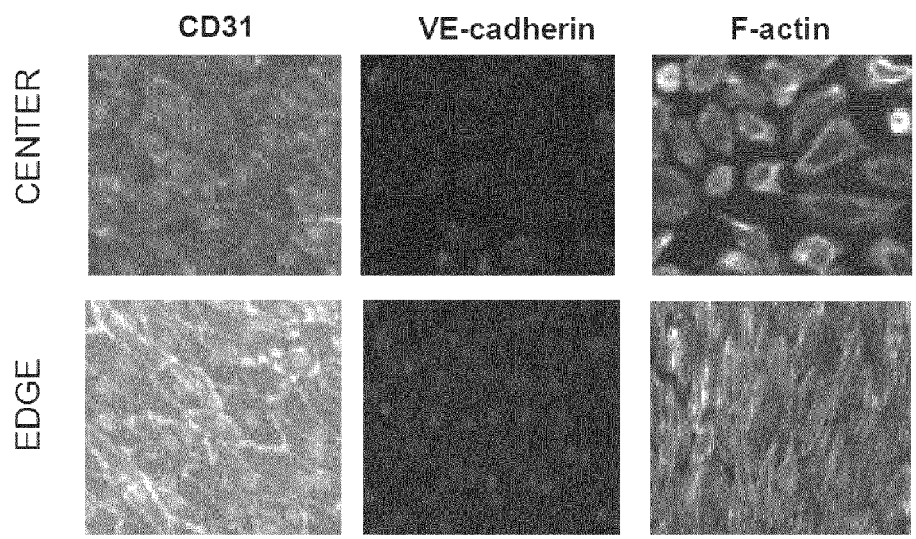
C
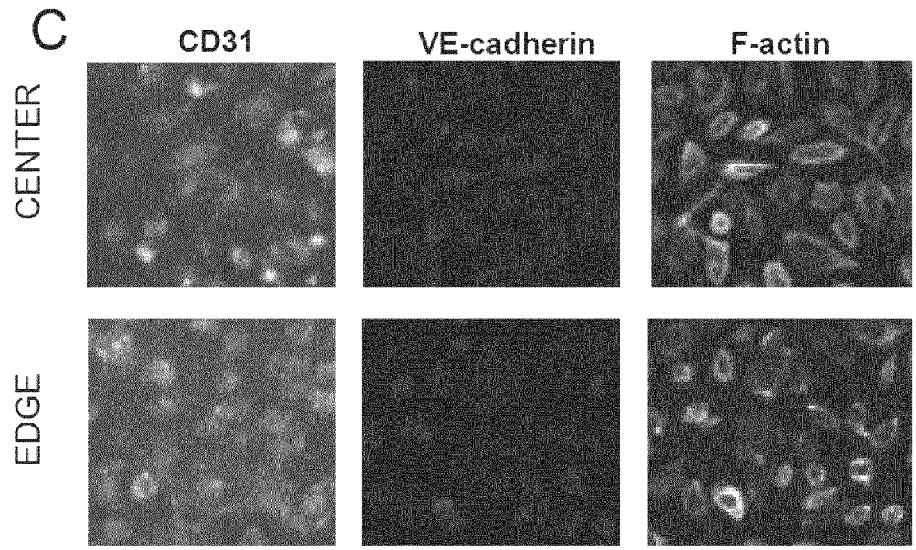

Figure 1D & E
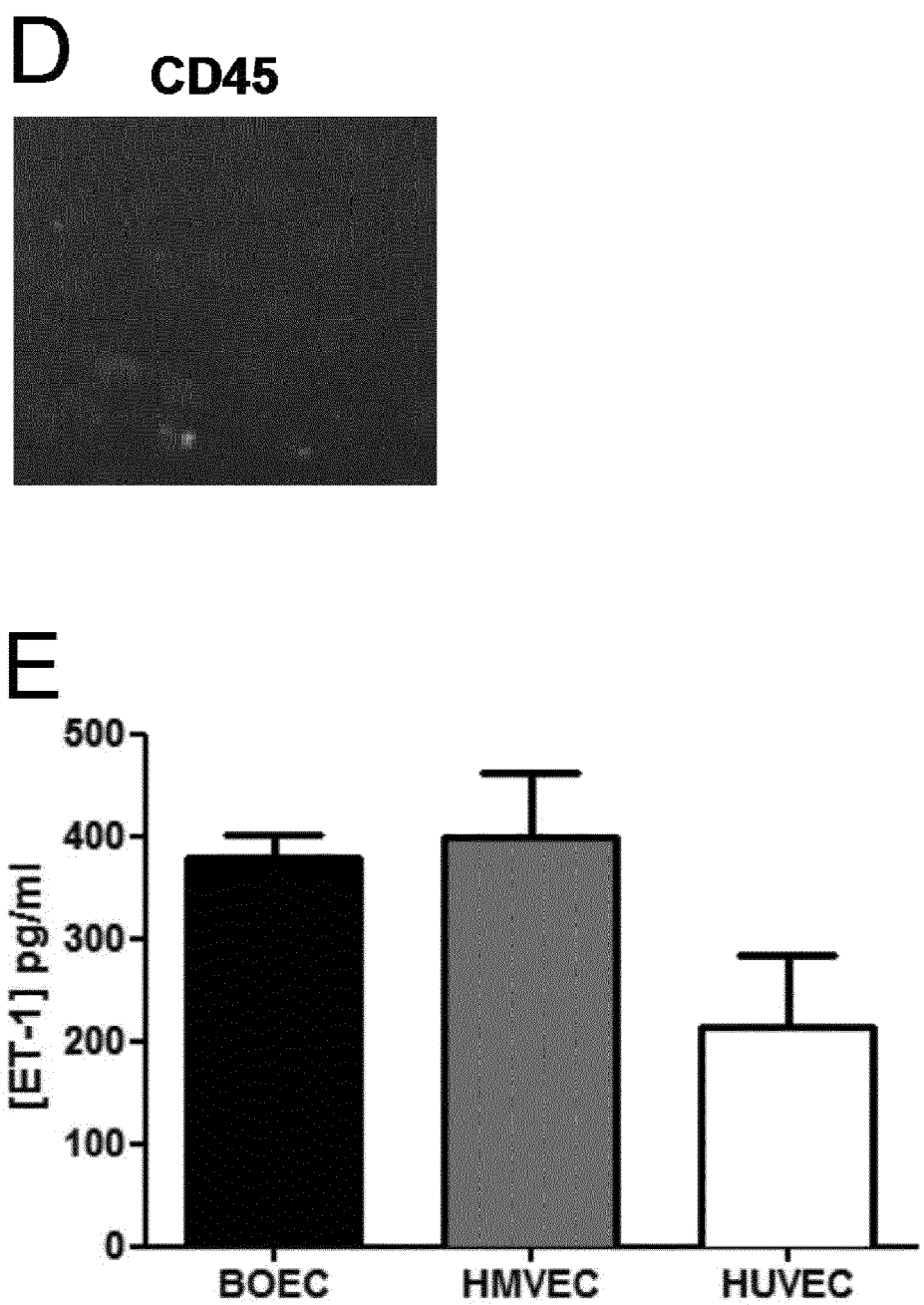

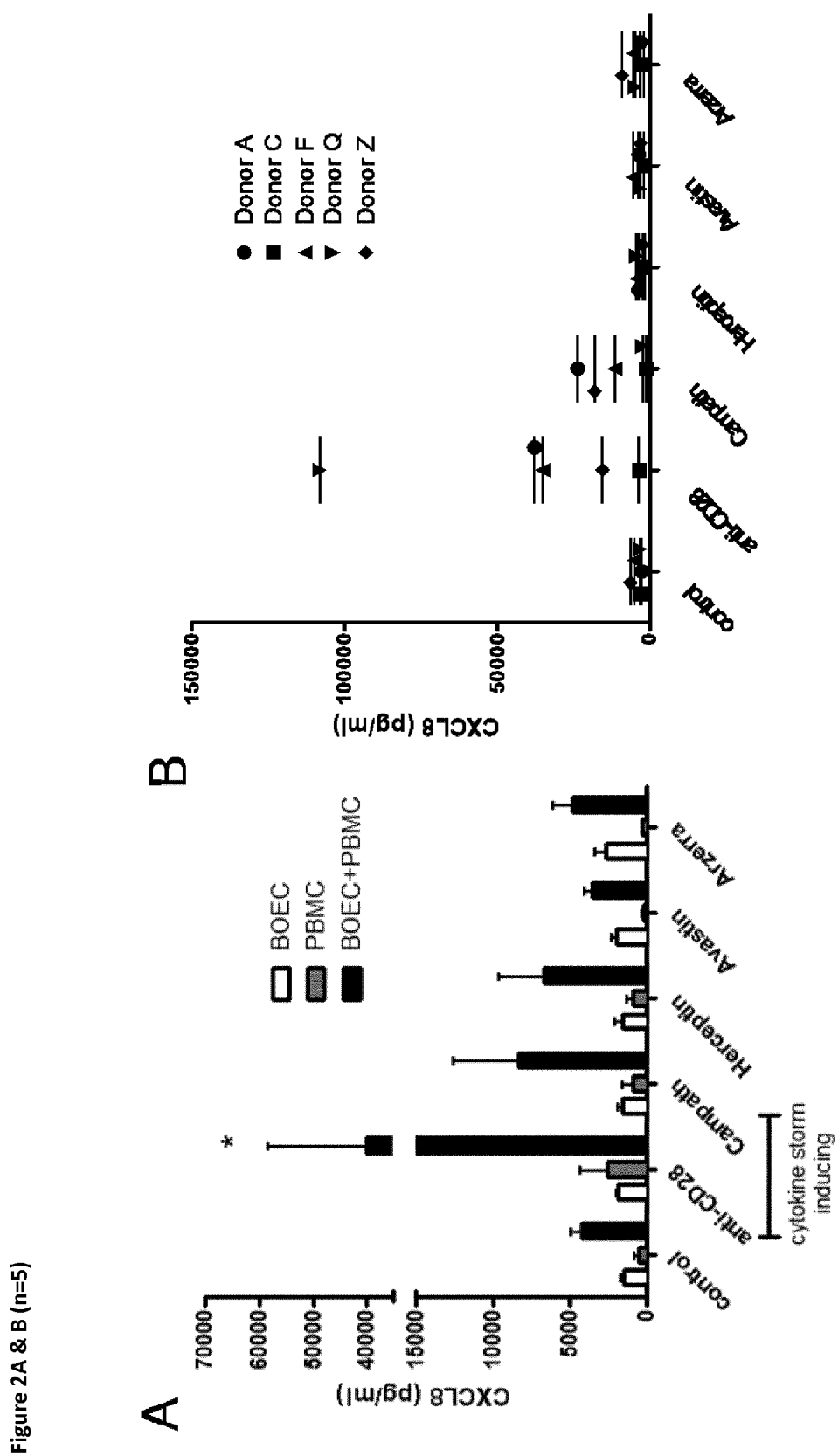
Figure 2A & B (n=5)

Figure 2C (n=8)
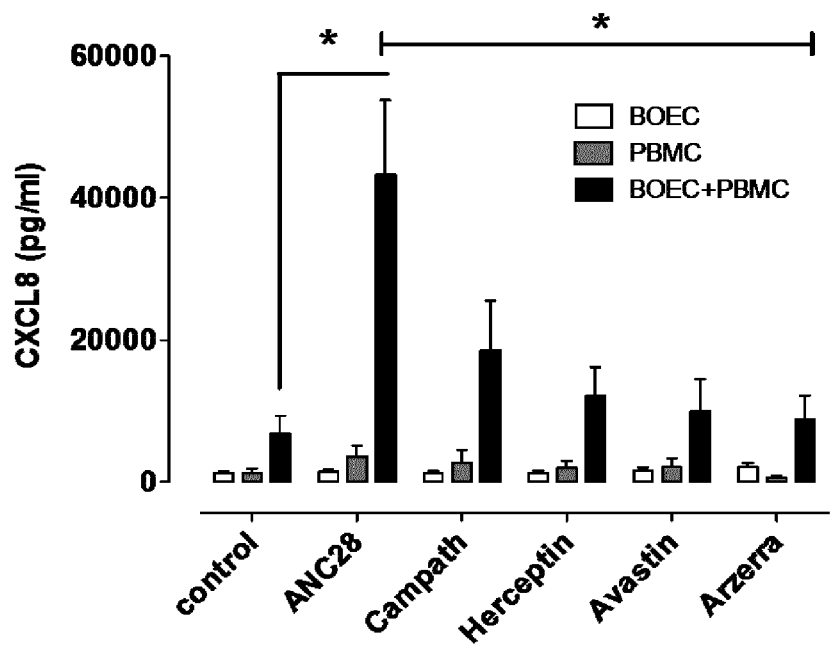
Figure 3A  A Mixed BOEC Assay (i.e. unmatched)
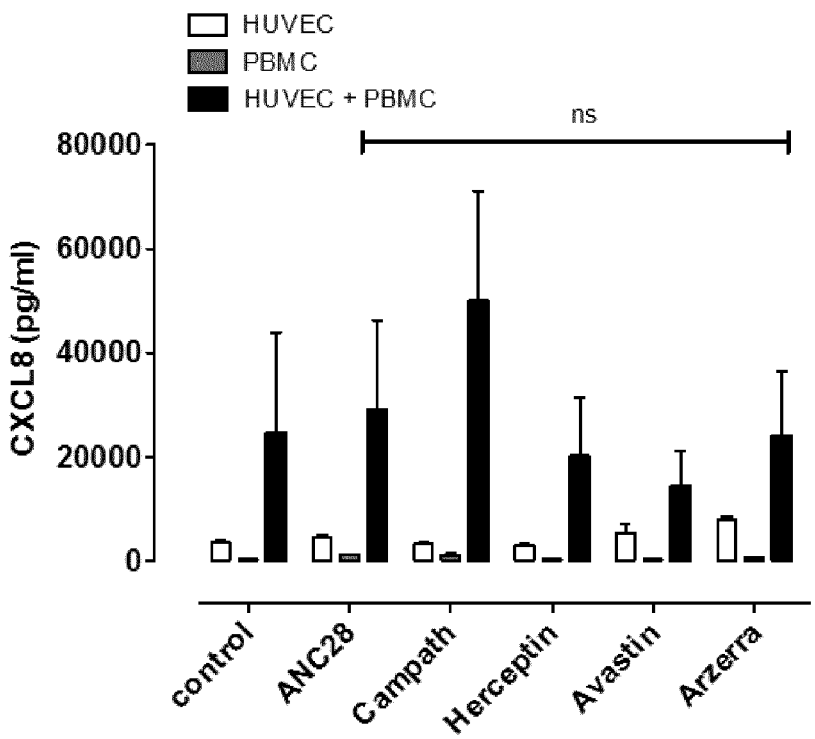

Figure 3B    A Mixed BOEC Assay (i.e. unmatched)
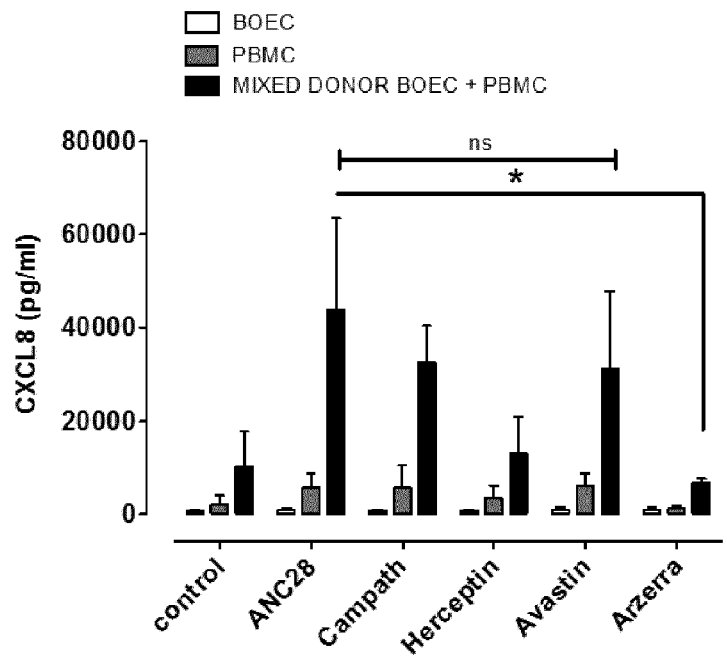
Figure 4
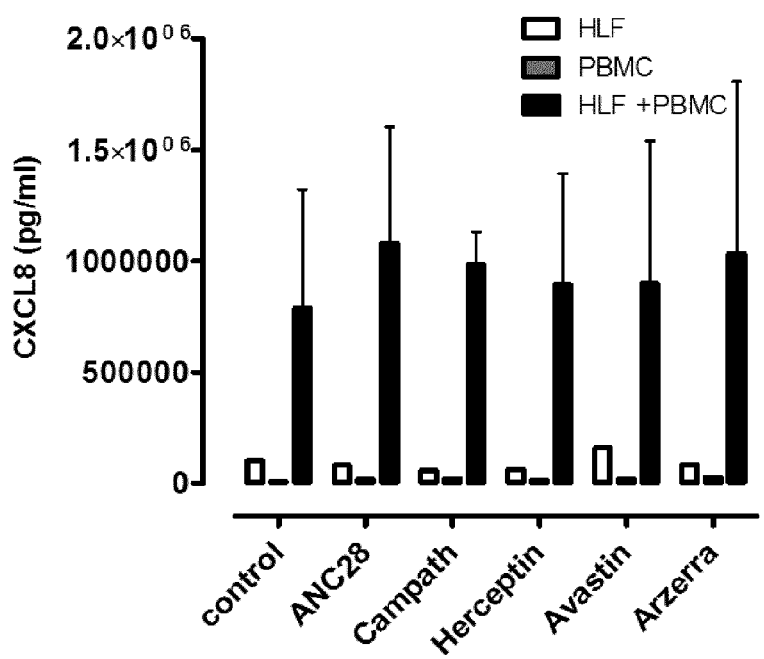

Figure 5B
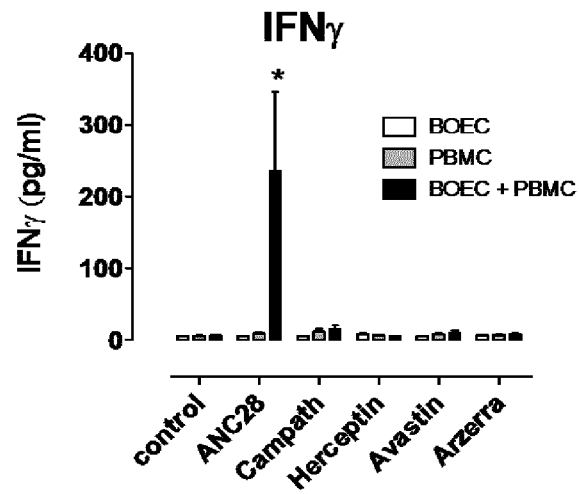
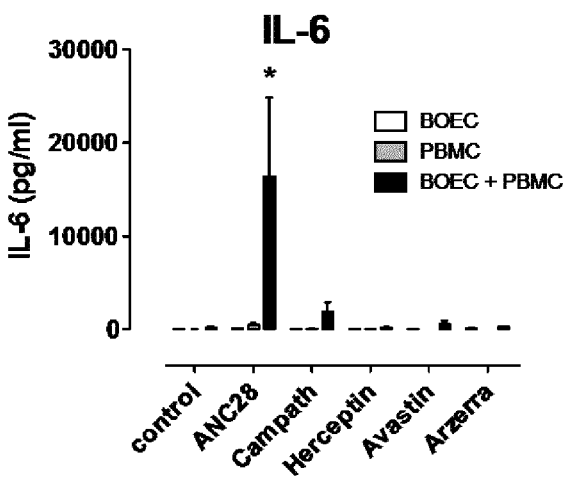
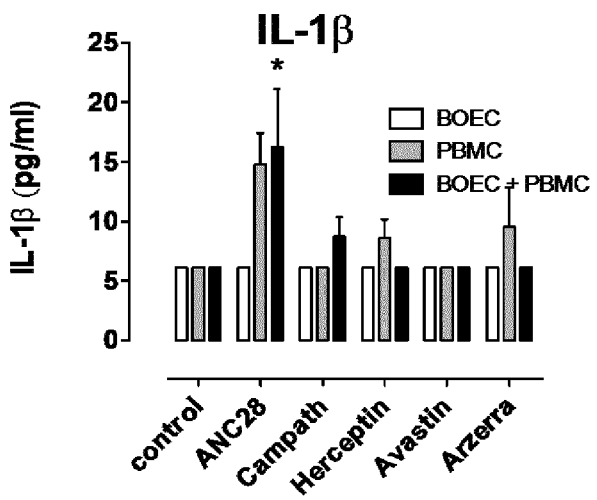

IN VITRO METHOD FOR ASSESSING CYTOKINE STORM RESPONSES

The present disclosure relates to an improved method for predicting in vitro the potential of a test compound, in particular putative biological therapeutic agents, to cause an adverse cytokine and/or cytokine storm response (also referred to as CRS) in a human patient.

In March 2006 severe adverse events occurred in a healthy human volunteer trial held at Northwick Park hospital involving the biologic therapeutic agent TGN1412. At least six volunteers from the trial were hospitalised because of adverse events after administration of the therapeutic agent and many of these had multiple organ dysfunction.

The volunteers were reported to have experienced cytokine release syndrome (also known as cytokine storm and cytokine release syndrome) resulting in angioedema, swelling of skin and mucous membranes, akin to the effects of the complement cascade in severe allergic reaction. The patients were treated with corticosteroids to reduce inflammation, and plasma-exchange to attempt to remove TGN1412 from their circulation. It was later confirmed that the volunteers had suffered from a cytokine storm, and that, paradoxically, their white blood cells had vanished almost completely several hours after administration of TGN1412.

TGN1412 had been tested in animals before administration to humans. However, it is believed that in the relevant respect the therapeutic agent elicited different response in humans than in laboratory animals. It has been hypothesised that the reaction seen in humans could have only occurred in animals with memory T cells. Whereas animals raised in laboratory conditions "sterile condition" have essentially no memory T cells and therefore do no illicit the same response. It now transpires that the animal species employed in laboratory studies simply have fewer memory T cells and thus don't illicit the same responses, so for example mice don't appear to illicit cytokine storm reactions. TGN1412 was also tested on isolated human T-cells and primates and there was no suggestion of the problems that were subsequently seen in humans. However, we now know that TGN1412 requires an endothelial cell (or other) interface in order to activate immune cells (see below).

Cytokine storm is where cytokine release by immune (and other) cells becomes excessive and damages the tissue and organs. In some patients the response is so severe it causes death.

The endothelium that lines the luminal surface of every blood vessel is the first cell of contact for activated circulating leukocytes. Interaction between the endothelium and leukocytes can result in profound amplification of inflammatory responses. Pioneering studies from Stebbings and others[1] suggests that this phenomenon is required in order to see a cytokine response to anti-CD28 superagonist TGN1412 in vitro from human peripheral blood mononuclear cells (PBMCs).

At present there exists a limited number of in vitro assays that can detect a cytokine response to an anti-CD28 superagonist such as TGN1412. These assays employ either a mixture of cellular components including:
  umbilical vein endothelial cells (HUVECs) and PBMCs[1],
  antibody immobilised (fixed; eg by allowing aqueous solutions of antibody to evaporate leaving the antibody/drug adhered to the surface structure) on plastic plates[1] or synthetic beads[2] before being added to PBMCs, or cultures of human whole blood[3].

It is clear that human tissue bioassays require a mixture of cellular components as evidenced by the findings that TGN1412 and related molecules do not activate isolated preparations of PBMCs or HUVECs, but when PBMCs and HUVECs are cultured together TGN1412 elicits a strong cytokine response[1,3,4]. However, the present inventor believes this type of bioassay and others reported in the literature are fundamentally flawed since they rely on the mixing of endothelial cells from one donor (in the case of HUVEC; foetal cells) and the PBMCs of another. Moreover, conventional mixed tissue bioassays do not appropriately delineate in some cases for some cytokines[3-5] antibodies such as TGN1412 that have a profound cytokine storm effect from those that cause, serious, but more mild and manageable responses such as Campath. Thus the results obtain in the state of the art cell based assays don't reflect adequately the same trends seen in in vivo responses to the same therapeutic agents.

This problem was investigated in a relatively recently paper Findlay et al[4] which states: "PBMC. HUVEC co-cultures did not fully reflect the reported in vivo measurements or immobilised TGN1412-stimulated release in vitro, indicating that there are alternative stimulatory mechanisms which trigger the release of the release of different cytokines" (page 142 col 1 first paragraph).

Findlay et al go on to hypothesise that this may be due to one or more of the following:
  1. "HUVEC are close to the senescence and are isolated from hypoxic vessel. Therefore, they may not provide the best model for endothelial interactions. Furthermore, endothelial cells from different organs and blood vessels exhibit considerable heterogeneity, and there could be tissue-specific characteristics not possessed by HUVEC which are required for maximal con-stimulation e.g, the highly endothelial venules which mediate adherence and migration of T cells in vivo.
  2. Cell types in addition to those present in HUVEC cultures are required for maximal stimulation.
  3. Low level production of IL-2 in co-cultures results in continuous consumption for driving T cell proliferation whereas in immobilisation assays, higher level production results in saturating levels and accumulation in the supernatant.
  4. Most likely a different mechanism of cytokine release occurs in the immobilisation assay compared to the co-culture, possibly involving different T cell subsets, and that additionally in the co-cultures, release of IL-6, IL-8 and TNFalpha occurs via a different mechanism to the release of IL-2 and IFNgamma e.g., IL-6 production by HUVEC in response to TNFalpha."

Point 2 was investigated in subsequent papers. Since 2006, those skilled in the art have been trying to address this problem and to date a suitable standard assay for general use, which is predictive of results in vivo, has not been identified.

This leaves a gap in the ability to test therapeutic agents for liabilities. Thus there is currently an urgent unmet need to develop a suitable human tissue testing assays that will, for example predict cytokine storm responses induced by biotherapeutics, such as TGN1412[6] and/or to test efficacy in the development of new drugs and small molecules as well as protein or stem cell based therapies that interact with immune pathways.

The present inventor has found an improved assay which seems to provide results analogous to those observed in humans administered TGN1412 and thereby meets a significant unmet need in the area of safety testing, in particular for biological drugs. The invention, unlike the current state of the art assay, also allows for direct testing of cell populations relevant to the in vivo clinical situation namely endothelial and PBMCs from patient target groups.

Whilst the prior art assays can be used to demonstrate a cytokine signal to TGN1412 it is hypothesised by the present inventor that because of the prior art assays employ cells from non-matched donors, they are susceptible to producing false positive and false negative responses. The latter may result from the mixing of tissue from non-matched donors, which can activate/inhibit immune responses native to each individual donor. This is illustrated by recent data from the inventor showing that in a whole blood/HUVEC mixed tissue bioassay there was a profound inflammatory activation seen using blood of at least 10% of donors[3].

It is not really possible to match HUVEC cells with the other tissue, such as PBMCs, employed in the assay and so an alternative system was required.

SUMMARY OF THE INVENTION

The present disclosure provides an in vitro method of assaying the stimulation of a cytokine storm response comprising the steps of:
a. co-culturing PBMCs and matched differentiated endothelial cells to provide a system representative of human responses in vivo, and
b. exposing the co-cultured cell system to a test agent,
c. analysing the system for the presence of one or more cytokines released after exposing the co-culture system to said test agent, and
optionally evaluating the response to the test agent in comparison to a response to one or more control agents.

The present inventors have established that BOECs (blood outgrowth endothelial cells) can be prepared from a blood sample and PBMCs can also be prepared, for example from the same sample (or another blood sample from the same donor) for use in the assay disclosed herein.

Advantageously the present inventor has found that this assay system is predictive of the in vivo responses and is likely to be a powerful tool in research and pharmaceutical safety evaluations. In comparison studies with the current industry standard assay, which utilises HUVEC and PBMC co-cultures or human whole blood, which is unmatched, the inventor has found that the assay according to the present disclosure more accurately predicts the 'rank order' of some drugs to cause cytokine storm reactions.

The inventor has also shown previously that, by contrast to BOECs, endothelial cells derived from other types of stem cells (namely embryonic stem cell—derived endothelial cells; hESC-EC) have a profoundly compromised immunological response[8] which would render them unsuitable predictors of cytokine storm responses in any type of in vitro cell based assay.

Importantly the bioassay according to the represent disclosure (BOEC plus PBMC, but not either cell type alone) does not detect a positive result for negative control antibodies which are given safely to patients and do not induce cytokine storm.

Advantageously the assay disclosed here may be employed to investigate the intensity of the cytokine response. Prior art assays, for example HUVEC co-culture assays are not capable being used in this way.

In addition when materials, for example BOECs and PBMCs are taken from a single subject, such as a human subject the assay can be used to investigate an individual persons' response to a given therapeutic agent or test agent.

Thus in one embodiment the assay disclosed herein can be employed in a personalised medicine context to predict the suitability of a therapeutic agent for a given human being.

DETAILED DESCRIPTION OF THE DISCLOSURE

An in vitro method as employed here is one performed completely outside a human or animal body using materials generally derived from a sample, such as human tissue and/or blood.

Cytokine storm (also referred to as hypercytokinemia) as employed herein is a potentially fatal immune response resulting from the inappropriate positive signalling between cytokines and immune cells and ultimately cytokine release. In patients this leads to a high fever, swelling and redness, extreme fatigue, nausea and in some instances is fatal. Whilst more than 150 known inflammatory mediators are thought to be released during cytokine storm, generally in the in vitro assay of the present disclosure one or more suitable cytokines are measured for example 1, 2, 3, 4, 5, 6, 7, 8, 9, 10 or more cytokines are measured, such as cytokines independently selected from IL-1β, TNFα, IL-6, IL-8 (CXCL8), IL-2, IL-10, IFNγ, IL-12p70 and GM-CSF (for example IL-6, TNFα, IFNγ, IL-2 and IL-8).

The readout for this assay is not limited to cytokines but could be any released factor that indicates cell activation and/or any cellular responses (e.g. proliferation) that indicates activation and/or inflammation.

Where only one cytokine is measured it may be especially appropriate to concomitantly include a positive control for cytokine storm in the assay to give a context to the response.

Thus in one embodiment the assay comprises one or more controls, for example a positive and/or negative control, such as a positive control, in particular an anti-CD28 superagonist, for example TGN1412- or ANC28 (such as TGN1412) and/or an anti-CD52 antibody, such as alemtuzumab (Campath), which cause cytokine responses in man and activate cells in the assay. In contrast antibodies such as the CD20 antibody Arzerra does not cause profound cytokine storm indiscriminately in man or activate co-cultures of cells in the assay.

ANC28 is a CD28 superagonist and one model for TGN1412 response. TGN1412 can employed in the assay according to the present disclosure and results obtained are equally predictive of CRS responses.

In one embodiment the assay may be optimised for a given superagonist employed, perhaps as a control, in the assay, for example ANC28 may be employed with media as per the examples described herein.

TGN1412 may be employed with media containing about 2% human serum.

The person skilled in the art is well able to tweak and optimise the conditions for a given system in relation to media and serum using only routine techniques.

PBMCs are easy to obtain from blood donated by volunteers.

Matched differentiated endothelial cells as employed herein refers to endothelial cells which are, blood matched, HLA matched, sex matched or fully matched with the PBMCs. Fully matched as employed herein means autologous i.e. the PBMCs and the endothelial cells are from the same donor.

In one embodiment the PBMCs and endothelial cells are derived from the same sample from a single donor.

Differentiated endothelial cells described here have been shown by the inventors to behave, in key ways, like endothelial cells from mature vessels. These include (i) aligning in the direction of shear stress, (ii) release of the endothelial cell hormones endothelin-1 and (iii) expression of the endothelial cell markers (for example CD31 and VE-cadherin).

Thus "differentiated endothelial cells" as employed herein is a cell that behaves in one or more key ways like endothelial cells from mature vessels, for example aligning in the direction of shear stress, releasing an endothelial cell hormone, such as endothelin-1, and/or the expression of one or more endothelial cell markers, such as CD31 and/or VE-cadherin.

PBMC as employed herein refers to the peripheral blood mononuclear cells. In one embodiment the PBMC employed in the method are in whole blood, i.e. are not isolated. In one embodiment isolated PBMCs are employed in the method.

Endothelial cells on blood vessels are inaccessible and can only be obtained from tissue removed in surgery or post mortem. Thus in one embodiment the endothelial cells are from a tissue cell, for example a biopsy.

However, conveniently endothelial cells grown out from progenitor cells (so called blood outgrowth endothelial cells; BOEC[9-11]) may be employed in the assay of the present disclosure. This is advantageous because it allows the cells in the assay to be matched in a convenient and simple way because these cells can be grown from a blood sample and so post mortem tissue and cell bank material (such as HUVECs) are not required.

BOEC are thought to originate from a progenitor cell in the circulation and might be involved in vessel growth repair[9]. Nonetheless, when grown in vitro, these cells have a clear endothelial cell phenotype and can be used to study endothelial cells from patients and provide new information on disease[11,12] and, putatively, as in the present disclosure, patient responses to drugs when grown in co-culture with autologous PBMCs.

BOEC as employed herein refers to differentiated endothelial cells cultured from populations in human blood or other bodily sources.

Described in the art are a number of ways of culturing BOECs. The exact method of culturing the BOECs including the length of culturing can be varied provided the differentiated endothelial phenotype is exhibited by the cells employed in the assay. A good visual indication of this phenotype is cobblestone shape/morphology discussed below and which skilled person will recognise.

Further suitable sources for endothelial include somatic cells.

In one embodiment the endothelial cells are prepared from pluripotent stems cells, which are induced to differentiate into endothelial cells.

The present inventors have characterised these cells as having classical hallmarks of native endothelium and, importantly, performed proof of concept experiments, which show that, in the presence of same donor PBMCs, BOEC respond avidly to an anti-CD28 super agonist.

In one embodiment the endothelial cells can be cultured to provide a phenotype which is characterised as elongated and aligned, for example to confirm their identity, perhaps as a quality control step. This culture is performed under complex shear conditions[13].

However, generally the cultured endothelial cells employed in the assay of the present disclosure have an appearance which is described as cobbled, for example as shown in the Figures. This is because they are cultured under 'static' culture conditions.

In one embodiment the endothelial cells are grown as a confluent layer in a vessel, for example a well in a plastic plate or vessel employed in a laboratory.

The number of cells may, depending on the context, be a relevant consideration, for example if the space in the vessel is limited.

In one embodiment 5,000 to 50,000 endothelial cells are employed per test sample (per therapeutic agent tested), for example 10,000, 15,000, 20,000, 25,000, 30,000, 35,000, 40,000 or 45,000.

Co-cultured as employed herein is wherein the endothelial cells and PBMCs are cultured for a period in the presence of each, i.e. in physical contact. In one embodiment the PBMCs are added to a culture of endothelial cell after a period of about 24 hours.

In one embodiment co-culturing can be employed in autologous serum, that is serum from the blood sample from which the PBMC and optionally the endothelial cells were obtained.

In one embodiment the cells are co-cultured in the presence of a matrix protein, for example fibronectin, gelatin, matrigel, collagen or similar.

In one embodiment the co-culture is performed in the absence of a matrix protein.

In one embodiment the analysis for cytokine releases is performed at one or more timepoints 1 to 36 hours after addition of the test agent, for example 1, 2, 3, 4, 5, 6, 7, 8, 9, 10, 11, 12, 13, 14, 15, 16, 17, 18, 19, 20, 21, 22, 23, 24 hours after addition of the test agent.

In one embodiment step b) of the method according to the present disclosure further comprises exposing the co-cultured cell system to an agent which induces cytokine storm in the system, followed by the exposure of the system to a test inhibitor of the induced response. Known inhibitors of cytokine storm include OX40 inhibitors. In one embodiment the assay may include a control inhibitor such as an OX40 inhibitor.

Thus, in one embodiment the method of the present disclosure may comprise a further step of identifying an inhibitor of cytokine storm in the in vitro co-cultured cell system disclosed herein. The method further comprises one or more of the following steps, developing and testing said compound further, formulating the compound, seeking regulatory approval for the compound for a pharmaceutical use, marketing and selling the compound and administering the same to a patient in need thereof. The further extends to the direct product of the method i.e. an inhibitor of cytokine storm identified from the method.

The disclosure herein also extends to use a data generated in a method described herein to support a regulatory submission, for example and IND or NDA submission or an equivalent process in another territory or country.

In one aspect there is provided an in vitro method of co-culturing PBMCs with matched differentiated BOEC and a cell population obtained or obtainable therefrom.

In one aspect there is provided an endothelial cell populations derived from BOEC for use in a matched bioassay according to the present disclosure.

Also provided is a kit comprising a co-culture system of PBMCs and matched differentiated endothelial cells representative of human cytokine storm responses in vivo.

A further aspect of the present disclosure is use of a co-culture system of PBMCs and matched differential endothelial cells suitable for use in an in vitro assay bioassay representative of human cytokine storm responses in vivo.

EXAMPLES

Anti-CD28 as employed in the examples is generally referring to ANC28. The latter is a commercially available antibody.

Some figures presented herein have been adjusted to show results of 0 equal to the limit of detection of the instruct because the sample being analysed is 1 in 10 dilution and this "correction" is accepted as appropriate in that situation.

FIG. 1A-G BOEC colonies emerged from PBMC co-cultures 5-20 days post-plating on collagen coated plates (shown day 8; no colonies (A; left) and day 16 when colonies emerged (A; right). BOEC expressed CD31, VE-cadherin and F-actin nuclei are stained with DAPI (b,c) when culture for 4 days under conditions of shear stress (B) and aligned at the edge of the well where flow is uni-directional/lamina (B; edge) but not at the centre where flow is non-directional/non-lamina (b; centre). BOEC were also grown under static conditions and expressed CD31, VE-cadherin and F-actin (C). BOEC did not express CD45 (D). BOEC when cultured for 24 h with Lonza-EGM2+10% FBS released endothelin (ET)-1 (E) and were compared with HUVEC and human lung micro-vascular endothelial cells) HMVEC in similar conditions. Data are mean±SEM (BOEC n=8) (HMVEC n=4) (HUVEC n=6).

FIG. 2 BOEC plus PBMC mono and co-culture bioassay data. PBMCs were added to matched BOECs. PBMCs were added to matched BOEC after 24 h. For monocultures vehicle media was added in place of PBMCs. At the same time cultures were treated +/− vehicle, ANC28 (ANC28. 1/5D10; TGN-like superagonist) (10 µg/ml), Campath (10 µg/ml), Avastin (10 µg/ml) or Arzerra (10 µg/ml) for 24 h. Data are mean±SEM (A-C; n=5 from 5 donors of BOEC and PBMC). (A) Shows the combined data with responses of all donors averaged. (B) Data from experiments where PBMCs and BOECs were treated in co-culture from the same individual are shown separated by donor on FIG. 2B and referred to as 'donor' A, donor C, donor F, donor Q and donor Z. (C) Data for individual donors for all assay conditions are shown in a separate graph for clarity. Statistical significance between treatments was determined by one-way ANOVA followed by Bonferroni's Multiple Comparison test (*p<0.05)(shown in A,B) and between mono/co-cultures by two-way ANOVA (*p<0.05) followed by Bonferronis post test.

Patient C was subsequently retested using the MSD assay and did show signs of the cytokine responses after exposure to the CD-28 superagonist.

Notably not all donors responded in to the same extent to the CD-28 superagonist. This showing the assay can be employed to assess the vigor/strength of the patient reaction to the proposed therapy.

The data is also presented in 2C with an n=8 (i.e. analysis of a larger number of samples and a the new analysis for donor C).

FIG. 3A-B HUVEC (A) and mixed donor BOEC (B) plus PBMC mono and co-culture bioassay data. PBMCs were added to HUVEC (A) or BOEC from different donors (B) after 24 h. For monocultures vehicle media was added. At the same time cultures were treated +/− vehicle, ANC28 (TGN1412-like superagonist) (10 µg/ml), Campath (10 µg/ml), Avastin (10 µg/ml) or Arzerra (10 µg/ml) for 24 h. Data are mean±SEM (A; n=3) (B; n=3). Statistical significance between treatments was determined by one-way ANOVA followed by Bonferroni's Multiple Comparison test (*p<0.05)

FIG. 4 Non-endothelial cell (human lung fibroblast (HLF)): PBMC mono and co-culture bioassay data. PBMCs were added to HLF. For monocultures vehicle media was added. At the same time cultures were treated +/− vehicle, anti-CD28 (TGN-like drug ANC28) (10 µg/ml), Campath (10 µg/ml), Avastin (10 µg/ml) or Arzerra (10 µg/ml) for 24 h. Data are mean±SEM (n=2 from 2 isolations).

Figure 5C:
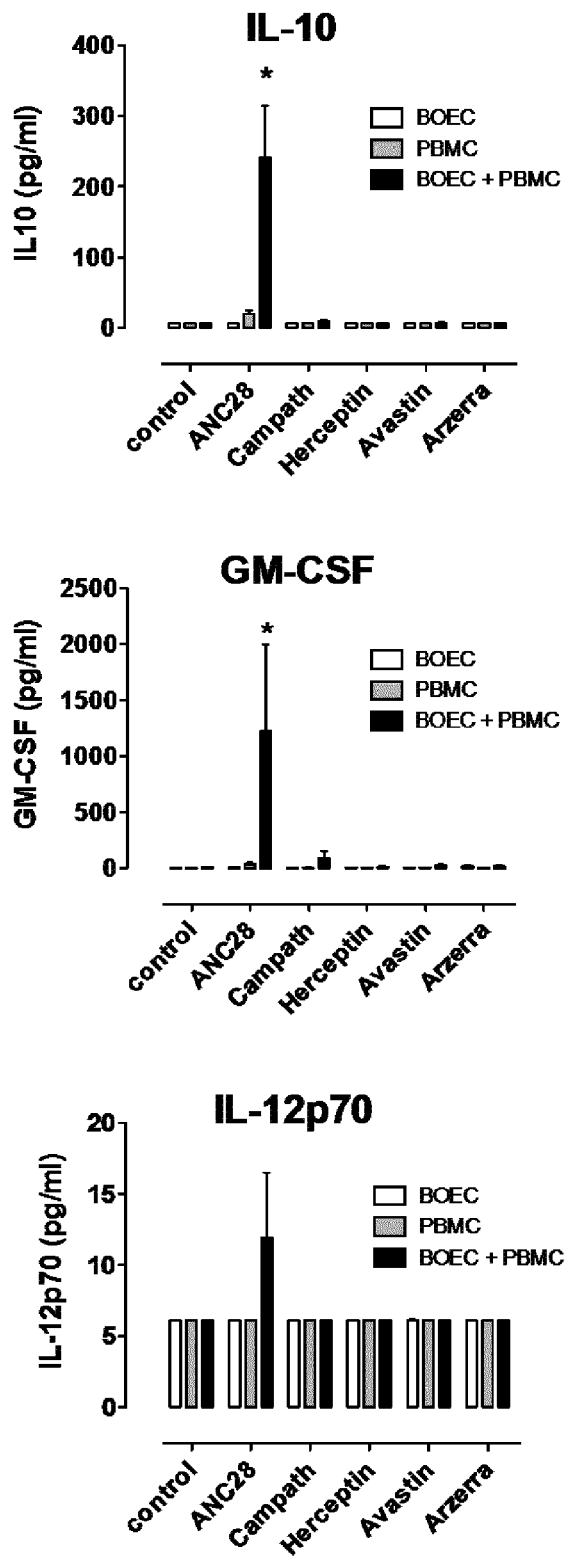

FIG. 5A-C Cytokine release data from MSD analysis. Measurements were carried out using an MSD 10-spot 9-plex Pro-Inflammatory Assay (see methods). Data are mean±SEM (n=5 from matched 5 donors). Statistical testing was carried out between 5 donors by one-way ANOVA followed by Dunnett's multiple comparison test comparing responses with drug to respective control only (*p<0.05).

MATERIALS AND METHODS

Media and Solutions:

Lonza-EGM2 media was prepared by addition of Lonza-EGM2 SingleQuot supplements and growth factors to Lonza-EBM2 basal medium (Lonza, Belgium). Information of the concentrations of additions in 'SingleQuot supplements and growth factors' are not available, however; suppliers information states the following are included; hEGF, gentamicin-amphotericin-B 100, R3-IGF-1, ascorbic acid, VEGF, hFGF-B, heparin, hydrocortisone. The media preparation was modified as the supplier FBS was discarded and replaced with 50 ml FBS (Hyclone HYC-001-330Y) to give Lonza-EGM2 10% FBS. All supplements were added separately to the medium. Media was aliquoted for daily use and stored at 4° C. away from light sources.

Type-1 rat tail collagen solution was prepared in 0.02N glacial acetic acid according to manufacturer's instructions at a concentration of 50 µg/ml. Plate and flask surfaces used for BOEC isolation and maintenance were coated with 5.2 µg/cm$^2$ collagen solution and incubated at 37° C., 5% $CO_2$ for 1 h prior to washing three times with PBS and addition of media/cell solutions/suspensions.

Isolation of Blood Outgrowth Endothelial Cells:

BOEC were isolated as published elsewhere[12] with minor modifications. Briefly, blood (48 ml) was collected from healthy volunteers (ethics code: 08/H0708/69) and PBMCs prepared. Tubes were inverted 8 times and then centrifuged at 1600RCF for 30 mins at room temperature with maximum acceleration and braking rates. Tubes were then inverted 8 times further to allow mixing of the buffy coat and plasma/serum fraction. This mixed fraction from 8 tubes was then carefully pooled into a 50 ml falcon tube and 10% FBS/PBS added to give a final volume of 50 ml. Cells were then centrifuged at 520 RCF for 10 mins with maximal acceleration and intermediate braking. The supernatant was discarded and pellets resuspended in 10 ml 10% FBS/PBS. This process was repeated a further two times giving three washes in total. Prior to the final centrifugation 10 µl of cell suspension was added to a haemocytometer for counting. After the final wash cells were subsequently resuspended to give 3-5×10$^7$/cells per well (4 ml) in Lonza-EGM2 with 10% FBS and added to collagen (BD, Oxford, UK) coated wells (see above) of a 6-well plate (Nunc, Denmark). Plates were incubated at 37° C., 5% $CO_2$. After 24 h media was carefully removed, cells were washed with Lonza-EGM2 10% FBS and 4 ml of fresh Lonza-EGM2 10% FBS added to each well. This process was repeated every 24 h for 4 d then every 24 h without washing until day 7. After day 7 media was replaced every other day without washing until colonies appear. Colonies of endothelial cells typically emerged between days 7-20. Once colonies emerged they were allowed to expand for not more than 4 days. Colonies were removed by trypsin (TrypLE 1×) digest using 2 ml trypsin/well. Trypsin was neutralised with 4 ml Lonza-EGM2 10% FBS and the 6 ml cell/trypsin mix collected in a 50 ml falcon tube and centrifuged at 190 RCF for 5 min at room temperature with maximal acceleration and intermediate break settings. Cells were then plated, expanded and maintained on T25 or T75 culture flasks (Nunc, Denmark) pre-treated with collagen as described above. Human umbilical vein endothelial cells used in this study were a gift from Professor Carloine Wheeler-Jones at the Royal Veterinary College, London.

Isolation and Culture of Human Peripheral Blood Mononuclear Cells:

Isolation of PBMCs is a standard laboratory protocol and can be done using a number of modified methods. Here peripheral blood samples (20 ml) were collected from healthy volunteers into 50 ml centrifuge tubes containing sodium citrate (ratio of sodium citrate:blood was 1:9). Citrated blood was diluted with RPMI:Lonza EGM2 media at 37° C. at a ratio of 1:1. Blood (6 ml) was layered on to Histopaque 1077 (Invitrogen, UK) (3 ml) and centrifuged at 400 RCF with maximal acceleration and minimal break setting for 30 min at room temperature. The peripheral blood cell buffy coat was carefully removed from each tube using a Pasteur pipette. PBMCs were transferred into 15 ml centrifuge tubes (up to 7 mls per tube) and made up to 14 mls with RPMI:Lonza EGM2 10% FBS (1:1). Tubes were centrifuged at 200 RCF for 15 min at room temperature to remove any remaining Histopaque. Supernatants were discarded from each tube. Cell pellets were pooled into a 50 ml falcon tubes with 20 ml of fresh media and centrifuged again at the same conditions for a final wash. Supernatants were removed and cell pellets resuspended in 1 ml of media and counted using haemocytometer. PBMC were seeded in 96-well plate with/without pre-plated BOECs at 70-80% confluence (Nunc, Denmark) at $1 \times 10^5$ cells/well.

Culture of Human Lung Fibroblasts:

Human lung fibroblasts were a gift from Dr Andrew Thorley and were maintained in Dubeccos modified eagle medium (DMEM; Life Technologies) with the following supplements penicillin-streptomycin (with 10,000 units penicillin and 10 mg streptomycin/ml in 0.9% NaCl) (Sigma, UK), L-glutamine (Sigma, UK), non-essential amino acids (Invitrogen, UK) and 10% FCS (Invitrogen, UK).

Dual Cell Autologous Assay Protocol:

For the dual cell assay, BOECs were isolated from healthy volunteers as described above. Once at passage 3 and confluent, cells were plated on 1% gelatin-coated 96-well plates (Nunc, Denmark) and allowed to adhere overnight. Patients were then re-called and PBMCs isolated as described above and added to the BOECs. Cytokine storm inducing drugs TGN-like anti-CD28 superagonist (ANC28. 1.5D10, referred to as ANC28) (10 μg/ml), Herceptin (anti-EGFR2: traztuzumab) (10 μg/ml) and Campath (anti-CD52: alemtuzumab) (10 μg/ml) were then added at day 0. Avastin (anti-VEGF$_4$: bevacizumab) (10 μg/ml) and Arzerra (anti-CD20: ofatumumab) (10 μg/ml) were included as negative controls for cytokine release induction. Plates were then incubated for 24 h. Supernatants were collected and stored at −20° C. for further analysis for ELISA and at −80° C. for MSD platform analysis.

Measurement of CXCL8:

CXCL8 (IL8) was measured by ELISA (Duoset CXCL8 Kit, DY208E; R & D Systems, Abingdon UK), according to manufacturer's instructions.

Cytokine Array Using MSD Platform:

To further analyse the cytokines released by matched BOEC and PBMC co-cultures as well as respective mono-cultures following stimulation with biologics an MSD (Meso Scale Discovery, USA) platform analysis was used. Human pro-inflammatory 9-Plex MULTISPOT 96-well-10 spot MSD plates were purchased from MSD (Gaithersburg, Md.) (Cat no. N05007A-1). Samples were diluted 1:10 in Lonza-EGM2 10% FBS/RPMI mix and added to the MSD plate. The immunoassay was carried out according to manufacturer's instructions. Plates were read using an MSC Sector Imager 2400 and analysed using MSD Discovery® Workbench software. Cytokines analysed were IL-2, CXCL8 (IL-8), IL-12q70, IL-1β, GM-CSF, IFNγ, IL-6, IL-10 and TNFα.

Statistical Analysis

Statistical analysis protocols were designed prior to experimentation. Analysis was carried out using GraphPad Prism5 software. Details of specific tests are given in figure legends.

Results

Characterisation of BOEC:

BOEC emerged from PBMC isolations of healthy volunteers in culture between days 7-20. As shown by others, BOEC displayed typical endothelial cell 'cobblestone' morphology (FIG. 1A) in static culture and expressed the requisite endothelial cell markers, CD31, VE-cadherin (FIG. 1B) but not the leukocyte common antigen CD45 (FIG. 1D). Endothelial cells from blood vessels have a typical phenotype response to shear stress. In order to further characterise BOEC as endothelial-typical, we grew them for 4 days under complex shear patterns. BOEC in the region of directional/laminar shear displayed the typical endothelial cell phenotype of being elongated and aligned (FIG. 1B) whilst those grown in regions of turbulent shear or under static were typically cobble stone in appearance (FIG. 1C-D). BOEC also released the endothelial peptide endothelin-1 (ET-1) at levels similar to endothelial cells from umbilical vein (HU-VEC) or the lung microvasculature (HMVEC) (FIG. 1E). BOEC in our study displayed these typical features.

Same Donor BOEC: PBMC Bioassay to Detect Cytokine Storm Inducing Biological Antibodies:

PBMCs released low levels of CXCL8 under control culture conditions. BOEC from the same donor released relatively more CXCL8 than PBMCs (FIG. 2). Co-culture of same donor BOEC and PBMCs had no discernable effect on levels of CXCL8 release when compared to levels released by either cell type alone under control conditions. For our same-donor endothelial cell: PBMC bioassay to be useful it should reveal a cytokine release to therapeutic antibodies known to cause cytokine storm in man, but not, to those used in man where cytokine responses seen are generally mild and do not limit the use of the therapy in man. In our proof of concept study we tested two positive control antibodies, a TGN1412-like anti CD28 superagonist (ANC28) and the CD52 antibody alemtuzumab (Campath). We tested three negative control antibodies, which are used therapeutically, but don't cause cytokine storm responses, these were (i) Herceptin, which binds to the human Epidermal Growth Factor Receptor 2; (ii) Avastin, which binds to vascular endothelial growth factor A and (ii) Arzerra which binds to CD20. PBMC or BOEC cultures alone did not respond to any of the antibodies tested when treated as mono-cultures. Similarly co-cultures of PBMCs and BOEC with Herceptin, Avastin or Arzerra did not release increased levels of CXCL8. However, co-cultures of PBMCs and BOEC released increased levels of CXCL8 when stimulated with the TGN1412—like anti-CD28 superagonist or with Campath where TGN1412>Campath. This correlates with the expected severity of cytokine storm for these drugs[5,16] (FIG. 2).

HUVEC or Mixed Donor BOEC Plus PBMC Mono and Co-Culture Assays:

In order to compare data from our same-donor assay with the current state-of-the-art assays[1,3,17], we ran parallel experiments using HUVECs as the detector endothelial cell model. PBMCs again released low levels of CXCL8 that was not increased by any of the biotherapetuics tested (FIG. 3A). HUVEC released relatively higher basal levels of CXCL8 that were not increased by anti-CD28 superagonist or Campath. HUVEC had a tendency to respond to the non-cytokine storm inducing drugs Avastin and Arzerra (FIG. 3A). The basis for these different results cannot be investigated further as HUVEC donors, unlike BOEC, cannot be easily traced and studied further. Similar results were found when PBMCs were added to BOECs from a different donor. Importantly, co-cultures of HUVEC and PBMC (from two donors) responded to TGN1412-like superagonist (ANC28) and Campath. This captures fully what is already know for this assay which, since the TGN1412 phase 1 trial, is as used as the gold standard assay to test biotherapeutics at the preclinical stage[1,17,18]. As we have recently shown using whole blood[3], in the current study we found that for one replicate of cells from one donor, the addition of PBMC to the HUVEC monolayer resulted in an activation of CXCL8 release which appeared to maximally activate the system and result in the assay being unable to detect cytokine storm. This immune activation response in control or other conditions is likely due to the mixing of tissue from different donors and is a serious limitation for the HUVEC or other similar assays, but one that is totally avoided by our 'same donor' assay.

Non-Endothelial (Human Lung Fibroblast): PBMC Assays:

To illustrate that interactions between cells to respond to TGN1412-like anti-CD28 superagonist was endothelial cell specific, and that endothelial cells were the ideal stem cell progeny for this kind of this assay, we ran the same assay using human lung fibroblasts as a platform. Human lung fibroblast released relatively higher levels of CXCL8 than PBMCs from two donors. Cytokine release was not increased in either cell type in response to treatment with any of the biologics tested. When cultured together, human lung fibroblasts and PBMCs are maximally activated to release CXCL8 and do not detect cytokine storm in response to any of the biologics tested (FIG. 4).

Further Analysis of Cytokine Storm Using the MSD Multiplex Platform:

To further assess the potential of this assay to accurately detect cytokine storm reactions we measured 9 cytokines (IL-2, IL-8, IL-12q70, IL-1β, GM-CSF, IFNγ, IL-6, IL-10 and TNFα) 7 of which (IL-2, IL-1β, IL-8, IL-6, IFNγ, IL-12p70 and TNFα) (FIG. 5A-C) were measured in patients displaying clinical cytokine storm when administered TGN1412 in 2006[16] and are key cytokines associated with cytokine storm. In our same donor BOEC: PBMC co-culture assay all cytokines accept IL-12p70 were increased in response to treatment with TGN1412-like anti-CD28 superagonist. Campath also showed a tendency to elevate release IL-8, IL-6 and GM-CSF in matched donor co-cultures. This data serves to i) validate our in house CXCL8 data using an ultra-sensitive MSD platform and ii) illustrate the power of the matched donor BOEC: PBMC co-cultures to detect cytokine storm to anti-CD28 superagonist and delineate this effect from less toxic drugs such as Campath and negative control antibodies such Avastin and Arzerra.

REFERENCES

1. Stebbings R, Findlay L, Edwards C, et al. "Cytokine storm" in the phase I trial of monoclonal antibody TGN1412: better understanding the causes to improve preclinical testing of immunotherapeutics. J Immunol 2007; 179:3325-31.
2. Walker M R, Makropoulos D A, Achuthanandam R, Van Arsdell S, Bugelski P J. Development of a human whole blood assay for prediction of cytokine release similar to anti-CD28 superagonists using multiplex cytokine and hierarchical cluster analysis. Int Immunopharmacol 2011; 11:1697-705.
3. Bailey L, Moreno L, Manigold T, et al. A simple whole blood bioassay detects cytokine responses to anti-CD28 (SA) and anti-CD52 antibodies. J Pharmacol Toxicol Methods 2012.
4. Findlay L, Eastwood D, Ball C, et al. Comparison of novel methods for predicting the risk of pro-inflammatory clinical infusion reactions during monoclonal antibody therapy. J Immunol Methods 2011; 371:134-42.
5. Eastwood D, Findlay L, Poole S, et al. Monoclonal antibody TGN1412 trial failure explained by species differences in CD28 expression on CD4+ effector memory T-cells. Br J Pharmacol 2010; 161:512-26.
6. Hünig T. The storm has cleared: lessons from the CD28 superagonist TGN1412 trial. Nat Rev Immunol 2012; 12:317-8.
7. Finco D, Grimaldi C, Fort M, et al. Cytokine release assays: Current practices and future directions. Cytokine 2014; 66:143-55.
8. Földes G, Liu A, Badiger R, et al. Innate immunity in human embryonic stem cells: comparison with adult human endothelial cells. PLoS One 2010; 5:e10501.
9. Yoder M C, Mead L E, Prater D, et al. Redefining endothelial progenitor cells via clonal analysis and hematopoietic stem/progenitor cell principals. Blood 2007; 109:1801-9.
10. Ingram D A, Mead L E, Tanaka H, et al. Identification of a novel hierarchy of endothelial progenitor cells using human peripheral and umbilical cord blood. Blood 2004; 104:2752-60.
11. Paschalaki K E, Starke R D, Hu Y, et al. Dysfunction of endothelial progenitor cells from smokers and chronic obstructive pulmonary disease patients due to increased DNA damage and senescence. Stem Cells 2013; 31:2813-26.
12. George P M, Oliver E, Dorfmüller P, et al. Evidence for the Involvement of Type I Interferon in Pulmonary Arterial Hypertension. Circ Res 2013.
13. Potter C M, Lundberg M H, Harrington L S, et al. Role of shear stress in endothelial cell morphology and expression of cyclooxygenase isoforms. Arterioscler Thromb Vasc Biol 2011; 31:384-91.
14. Martin-Ramirez J, Hofman M, van den Biggelaar M, Hebbel R P, Voorberg J. Establishment of outgrowth endothelial cells from peripheral blood. Nat Protoc 2012; 7:1709-15.
15. Thill M, Strunnikova N V, Berna M J, et al. Late outgrowth endothelial progenitor cells in patients with age-related macular degeneration. Invest Ophthalmol Vis Sci 2008; 49:2696-708.

16. Suntharalingam G, Perry M R, Ward S, et al. Cytokine storm in a phase 1 trial of the anti-CD28 monoclonal antibody TGN1412. N Engl J Med 2006; 355:1018-28.
17. Stebbings R, Eastwood D, Poole S, Thorpe R. After TGN1412: Recent developments in cytokine release assays. J Immunotoxicol 2012.
18. Dhir V, Fort M, Mahmood A, et al. A predictive biomimetic model of cytokine release induced by TGN1412 and other therapeutic monoclonal antibodies. J Immunotoxicol 2012; 9:34-42.

The invention claimed is:

1. An in vitro method of assaying the stimulation of a cytokine storm response comprising:
   (a) co-culturing peripheral blood mononuclear cells (PBMCs) and matched differentiated endothelial cells to provide a cell system representative of human responses in vivo;
   (b) exposing the co-cultured cell system to a test agent;
   (c) analyzing the system for presence of one or more cytokines released after exposing the co-culture system to the test agent; and
   (d) optionally evaluating the response to the test agent in comparison to a response to one or more control agents;
   wherein the endothelial cells are autologous to the PBMCs; and
   wherein the endothelial cells are derived from blood outgrowth endothelial cells.

2. The method of claim 1, wherein the endothelial cells are capable of being cultured to provide a phenotype; wherein the phenotype is characterized as elongated and aligned.

3. The method of claim 1, wherein the response of the test agent is evaluated in comparison to one or more control agents.

4. The method of claim 3, wherein the control agent is a TGN1412 anti-CD28 antibody or an anti-CD52 antibody.

5. The method of claim 4, wherein the anti-CD52 antibody is alemtuzumab.

6. The method of claim 1, wherein the analyzed cytokine is CXCL8.

7. The method of claim 1, wherein exposing the co-cultured cell system to a test agent comprises exposing the co-cultured cell system to an agent which induces cytokine storm in the system, followed by the exposure of the system to a test inhibitor the induced response.

8. The method of claim 7, further comprising identifying an inhibitor of cytokine storm in the in vitro co-cultured cell system.

9. The method of claim 4, wherein the endothelial cells are from a biopsy.

* * * * *